(12) United States Patent
Chinn et al.

(10) Patent No.: US 6,431,505 B2
(45) Date of Patent: Aug. 13, 2002

(54) IV POLE

(75) Inventors: Robert C. Chinn, Atlanta; James N. Chinn, Roswell, both of GA (US)

(73) Assignee: Ferno-Washington, Inc., Wilmington, OH (US)

( * ) Notice: Subject to any disclaimer, the term of this patent is extended or adjusted under 35 U.S.C. 154(b) by 0 days.

(21) Appl. No.: 09/816,581

(22) Filed: Mar. 23, 2001

Related U.S. Application Data (60) Provisional application No. 60/191,583, filed on Mar. 23, 2000.

(51) Int. Cl.[7] .............................. F16L 3/00; A47F 5/00; A47F 7/00; F16M 11/00; F16M 13/00
(52) U.S. Cl. ................. 248/121; 248/125.1; 248/122.1; 248/125.8
(58) Field of Search .............................. 248/121, 125.1, 248/122.1, 125.8, 159, 622, 100; 267/64.26, 119

(56) References Cited

U.S. PATENT DOCUMENTS

| | | | | |
|---|---|---|---|---|
| 3,835,486 A | * | 9/1974 | Benoit | 5/317 |
| 4,113,222 A | * | 9/1978 | Frinzel | 248/412 |
| 4,211,380 A | | 7/1980 | Lillegard et al. | |
| 4,262,872 A | * | 4/1981 | Kodet | 248/311.3 |
| 4,541,596 A | | 9/1985 | Price | |
| 4,592,527 A | * | 6/1986 | Karapita | 248/318 |
| 4,744,536 A | * | 5/1988 | Bancalari | 248/125 |
| 4,961,557 A | | 10/1990 | Garvin et al. | |
| 5,016,307 A | | 5/1991 | Rebar | |
| 5,078,349 A | | 1/1992 | Smith | |
| 5,094,418 A | | 3/1992 | McBarnes, Jr. et al. | |
| 5,135,191 A | | 8/1992 | Schmuhl | |
| 5,149,036 A | * | 9/1992 | Sheehan | 248/215 |
| 5,319,816 A | * | 6/1994 | Ruehl | 5/600 |
| 5,407,163 A | | 4/1995 | Kramer et al. | |
| 5,772,162 A | | 6/1998 | Lin | |
| 6,202,659 B1 | * | 3/2001 | Sachs | 135/20.1 |
| 6,224,561 B1 | * | 5/2001 | Swendson | 600/562 |
| 6,231,016 B1 | * | 5/2001 | Slone | 248/200 |

* cited by examiner

*Primary Examiner*—Kimberly T. Wood
*Assistant Examiner*—Amy Sterling
(74) *Attorney, Agent, or Firm*—Killworth, Gottman, Hagan & Schaeff LLP (57) ABSTRACT

IV pole having mounted at an upper end a holding assembly comprising a head and a plunger, and at a lower end a docking assembly. The head on an upper portion includes at least two opposed upwardly extending projections suitably for hanging IV fluid containers. The plunger is movable between an extended position in which the plunger is held a distance above the height of the projections, and a retracted position in which the plunger is proximate to the projections such that removal of IV fluid containers hung on the projections is prevented. The smooth profile of the head and plunger greatly reduces the risk of the IV pole getting snagged on an obstruction or causing injury to rescue personnel. The docking assembly permits the IV pole to be removably secured to a docking port provided to a structural member and to be lowered to a stowed position.

20 Claims, 11 Drawing Sheets

IV POLE

CROSS REFERENCE TO RELATED APPLICATIONS

This application claims the benefit of the following U.S. Provisional Application: Serial No. 60/191,583 for IV POLE, filed Mar. 23, 2000.

BACKGROUND OF THE INVENTION

This invention relates to an IV pole and, more particularly, to an IV pole with a holding assembly that safely secures intravenous fluid containers to the top of the IV pole.

Figure 1:
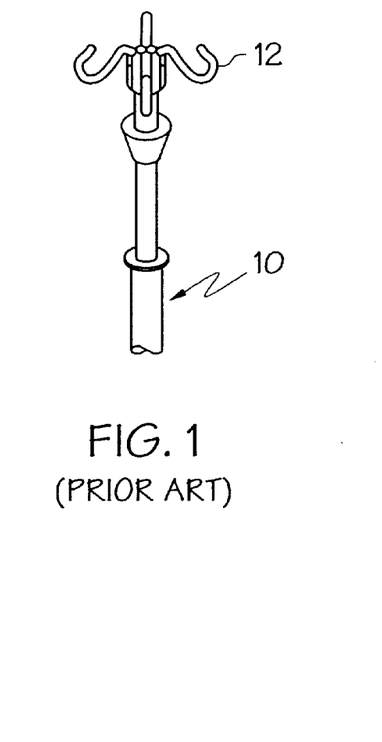
FIG. 1 is a perspective view of a first-type prior art holding assembly.
Figure 2:
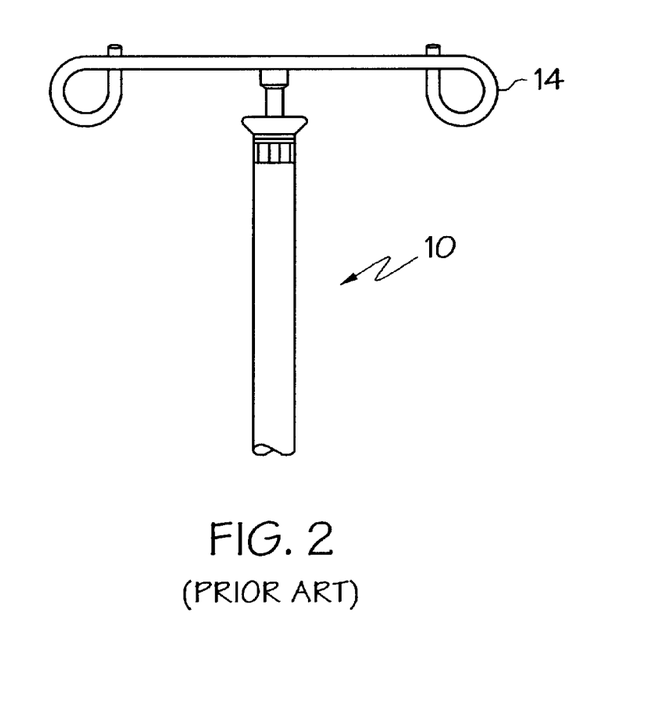
FIG. 2 is side view of a second-type prior art holding assembly.

Many varieties of IV poles exist in the field for supporting intravenous fluid containers to facilitate the gravity feed of fluids contained therein to patients oriented in an adjacent support structure, such as an emergency cot or bed. Two common types of IV support arms or brackets used to support or hang IV containers from a conventional IV pole 10 are illustrated by FIGS. 1 and 2. As shown by FIG. 1, the first common bracket-type is a hook assembly 12, such as disclosed by U.S. Pat. Nos. 5,095,418, and 5,407,163. The second common bracket-type is a looped wire assembly 14, such as disclosed by U.S. Pat. Nos. 5,135,191, and 5,772,162, and as shown by FIG. 2

In many instances, the IV pole 10 is mounted directly to an emergency stretcher. In that particular instance, having one of the above-mentioned common bracket-types 12 or 14 may cause the IV pole 10 to snag on an obstruction due to the protruding and/or hooked shape. As a result, a delay in evacuating a patient carried on the emergency stretcher may ensue if it is necessary to unhooking the bracket from the obstruction. Additionally, catching the bracket on an obstruction may result in damaging the IV fluid container hung thereon. Furthermore, having one of the mentioned bracket-types may cause physically injury to an inattentive technician, such as for example, by being caught in the eye with the bracket due to the bracket's protruding shape.

Accordingly, there is a need for an IV pole with a holding assembly that secures intravenous fluid containers thereon, and which minimizes the chances of the IV pole snagging on an obstruction.

SUMMARY OF THE INVENTION

The above-mentioned needs have been met by providing an IV pole comprising a holding assembly at a first end and a docking assembly at a second end. The holding assembly comprises a head and a plunger. The head on an upper portion includes at least two opposed upwardly extending projections. The projections are shaped and sized such that IV fluid containers may be hung thereon. A guide hole is provided by the head in the area of the upper portion between the projections. A lower portion of the plunger is mounted axially and slidably within the guide hole, wherein the plunger is movable between an extended position and a retracted position that secures the IV fluid containers to the IV pole. The smooth profile of the head and plunger greatly reduces the risk of the IV pole getting snagged on an obstruction or causing injury to rescue personnel. The docking assembly permits the IV pole to be removably secured to a docking port provided to a structural member of a structure supporting a patient. Additionally, the docking assembly permits the IV pole to be lowered to a stowed position, if desired.

In the extended position, an upper portion of the plunger is held a distance above the height of the projections to allow IV fluid containers to be hung upon the projections. Pushing downwardly on the plunger's upper portion vertically moves the plunger within the guide hole to place the plunger in a retracted position. In the retracted position, the underside of the plunger's upper portion is proximate to the projections such that removal of IV fluid containers hung on the projections is prevented. Various mechanisms, such as a spring or a diaphragm, may be used to maintain and/or move the plunger to the extended and retracted positions. Accordingly, in certain embodiments of the invention, the plunger may be manually and/or automatically moveable between the retracted and extended positions.

In accordance with one embodiment of the present invention, a holding device for securing at least one intravenous fluid supply to a fixture is provided. The holding device comprises a head having a proximate end portion configured to support the at least one intravenous fluid supply, and a distal end portion configured to be mounted to the fixture. The head defines an internal chamber and a guide hole provided in the proximate end portion, wherein the chamber is in communication with the guide hole. The holding device further comprises a plunger having a cap portion. The plunger slidably mounts within the chamber and extends through the guide hole. The plunger is operable between an extended position in which the cap potion of the plunger extends a distance above the proximate end portion of the head and a retracted position in which the cap portion secures the at least one intravenous fluid supply to the holding device.

In accordance with another embodiment of the present invention, an IV pole for supporting fluid containers above a structure is provided. The IV pole comprises an elongated pole having a first end and a second end, and a holding device mounted to the first end. The holding device has upwardly extending projections and a plunger with a cap portion. The plunger is movable between an extended position, in which the cap portion is a distance from the projection such that the fluid containers may be hung upon the projections, and a retracted position in which the cap portion is in close proximity to the projections such that the hung fluid containers are releasably secure upon the projections. The IV pole further comprises a support mounted at the second end for holding the IV pole in an upright condition.

In accordance with still another embodiment of the present invention, an IV pole for supporting fluid containers above a structure is provided. The IV pole comprises an elongated pole having a first end and a second, a collar with an integral dovetail base, a docking port provided to the structure and having an oppositely shaped channel configured to slidably receive the dovetail base of the collar. The collar releasably secured to the docking port. The IV pole further comprises a mounting plug having first and second ends, the first end of the mounting plug mounted to the first end of the pole, the second end of the mounting plug rotatably mounted to the collar such that the IV pole is movable between an upright condition and a stowed condition.

Other features and objects of the present invention will be apparent in light of the description of the invention embodied herein.

BRIEF DESCRIPTION OF THE DRAWINGS

The following detailed description of the embodiments of the present invention can be best understood when read in conjunction with the accompanying drawings, where like structure is indicated with like reference numerals and in which.

DETAILED DESCRIPTION OF THE PREFERRED EMBODIMENTS

Figure 3:
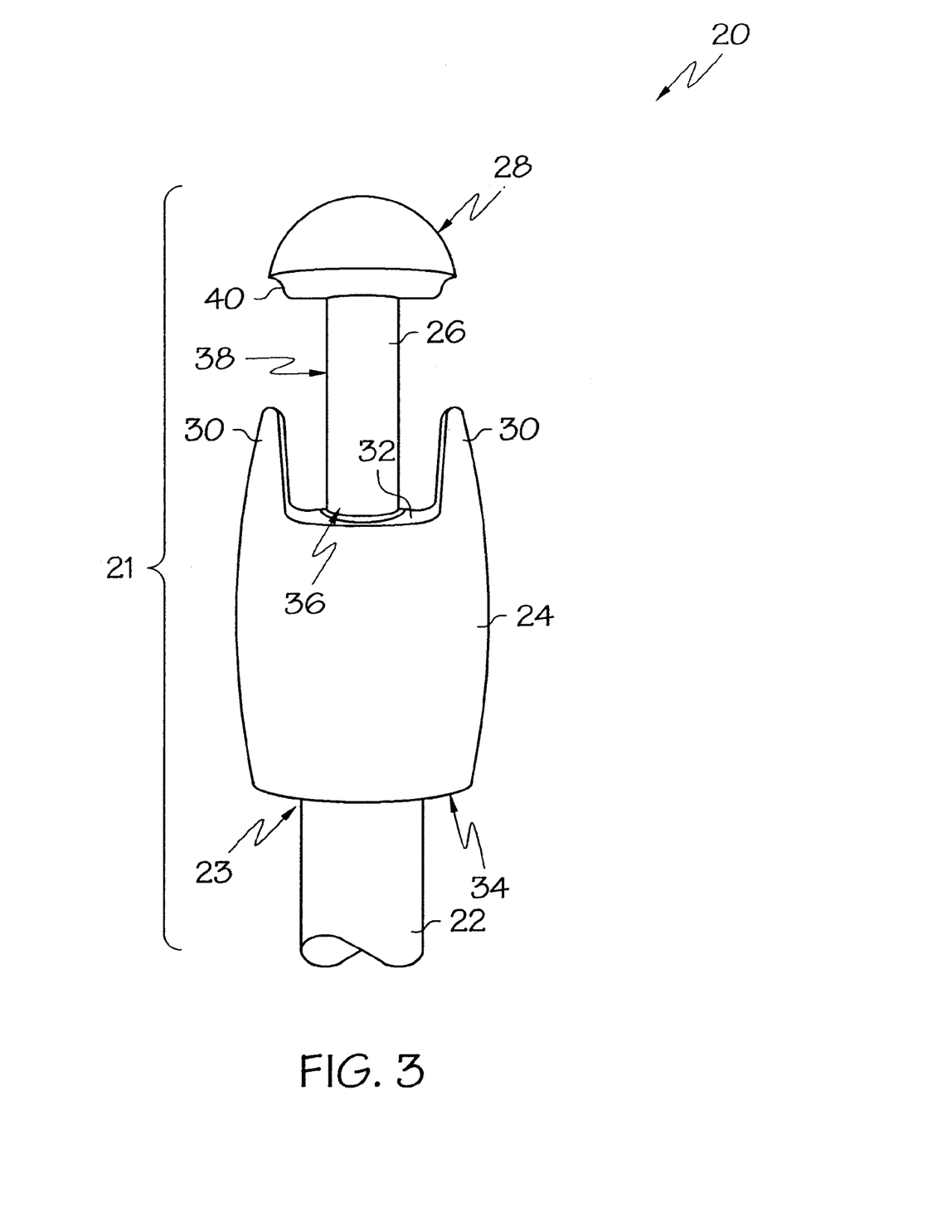
FIG. 3 is front view of an embodiment of a holding assembly of an IV pole according to the present invention shown in an open position.
Figure 4:
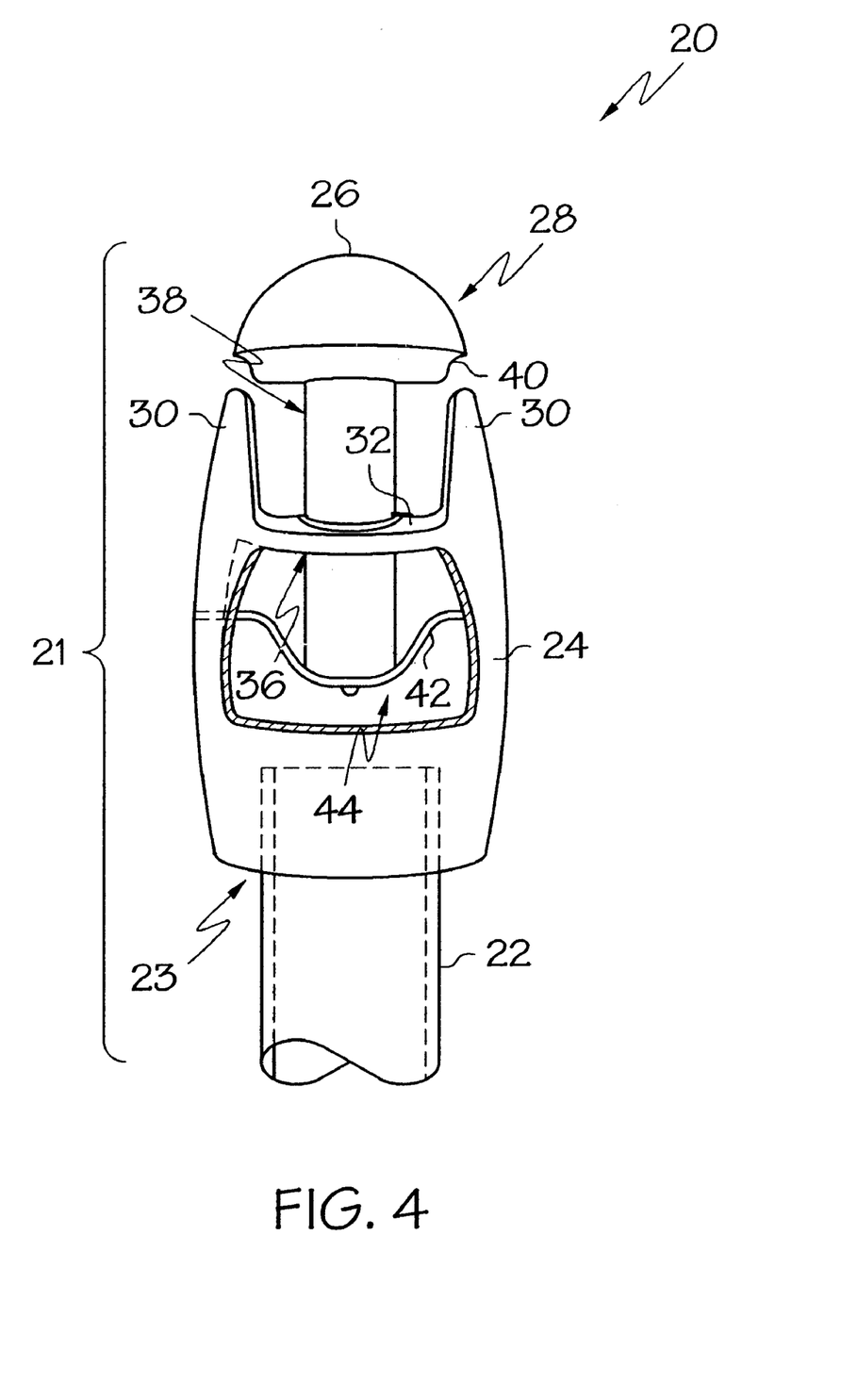
FIG. 4 is front view of the holding assembly of FIG. 3, partially cut away to show the internal components, and in a closed position.

With regards to FIGS. 3–11, various embodiments of a holding arrangement used to secure intravenous fluid containers to an IV pole 20 according to the present invention are discussed. Referring to FIG. 3, at a first end 23 of an elongated pole 22, a first embodiment of the holding device 21 includes a head 24, and a plunger 26 with a cap portion 28. The head 24 includes at least a pair of projections 30 opposed two each other and integrally formed with the head 24. The pair of projections 30 extends upwardly from a land area 32 of the head 24 and are shaped and sized to provide attachment points such that conventional IV fluid containers may be hung thereon. The head 24 further includes a butt portion 34 by which the head 24 mounts to the pole 22 with a tube and butt engagement, as illustrated by FIG. 4. Alternatively, the head 24 may mount to the pole 22 with a male and female engagement, wherein a male extension of the head 24 maybe inserted into the inner diameter of the pole 22.

A plunger guide hole 36 is formed within the land area 32 of the head 24 between the projections 30. A stem portion 38 of the plunger 26 is slidably mounted within the plunger guide hole 36, wherein the plunger is movable between an extended position, illustrate by FIG. 3, and a retracted position, illustrated by FIG. 4.

In the extended position, the cap portion 28 of the plunger 26 is held a distance above the height of the projections 30 to allow IV fluid containers to be hung upon the projections. Pushing downwardly on the cap portion 28, vertically moves the stem portion 38 of the plunger 26 within the plunger guide hole 36 to place the plunger in the retracted position. In the retracted position, a seating surface 40 of the cap portion 28 is proximate to the projections 30 such that removal of IV fluid containers hung on the projections is substantially prevented. It is to be appreciated that the holding device 21 provides for a safer holding arrangement due to the holding device's smooth circumferential profile and the protected vertical attachment points, which minimizes the chance of the upper portion of the IV pole 20 getting snagged on an obstacle during transport.

Various actuator mechanisms may be used to maintain and/or move the plunger 26 of the holding device 21 to the extended and retracted positions. In the embodiment of the holding device 21 illustrated by FIG. 4, showing the head 24 partially cut away, the plunger 26 is conventionally mounted at an end to a flexible membrane 42. The flexible membrane 42 is housed within a chamber 44 of the head 24 that is in communication with the plunger guide hole 36. The membrane 42 is flexibly deformable to an up position (not shown) and a down position as illustrated, which maintains the plunger 26 in the retracted position. Deforming the membrane 42 to the up position maintains the plunger 26 in the extended position illustrated by FIG. 3. Manually pushing or pulling on the cap portion 26 deforms the membrane 42, and situates the plunger 26 in the retracted and extended position, respectively.

Figure 5A:
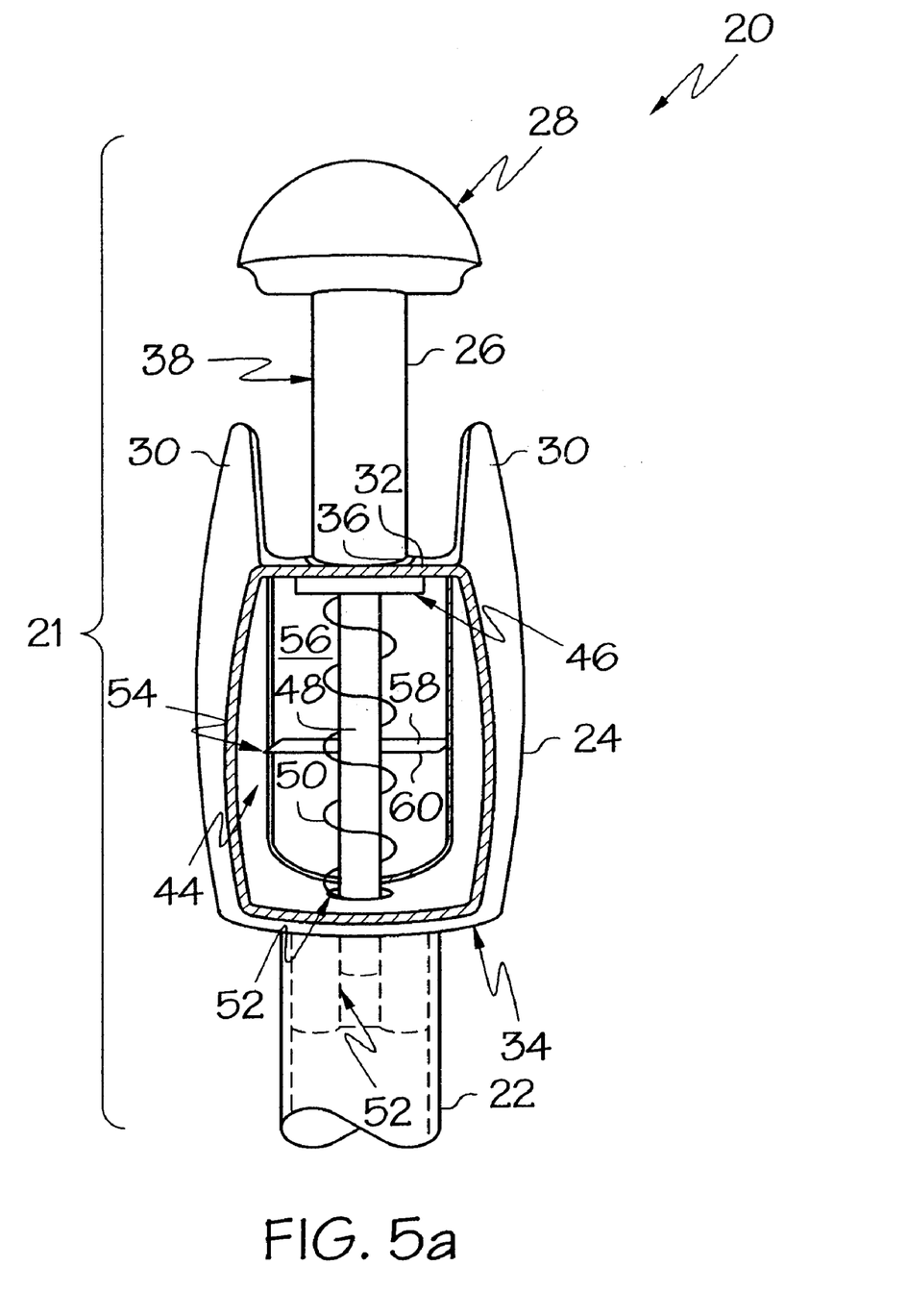
FIGS. 5a and 5b are back and side views, respectively, illustrating other embodiments of a holding assembly of an IV pole according to the present invention, and partially cut-away showing their internal components.
Figure 5B:
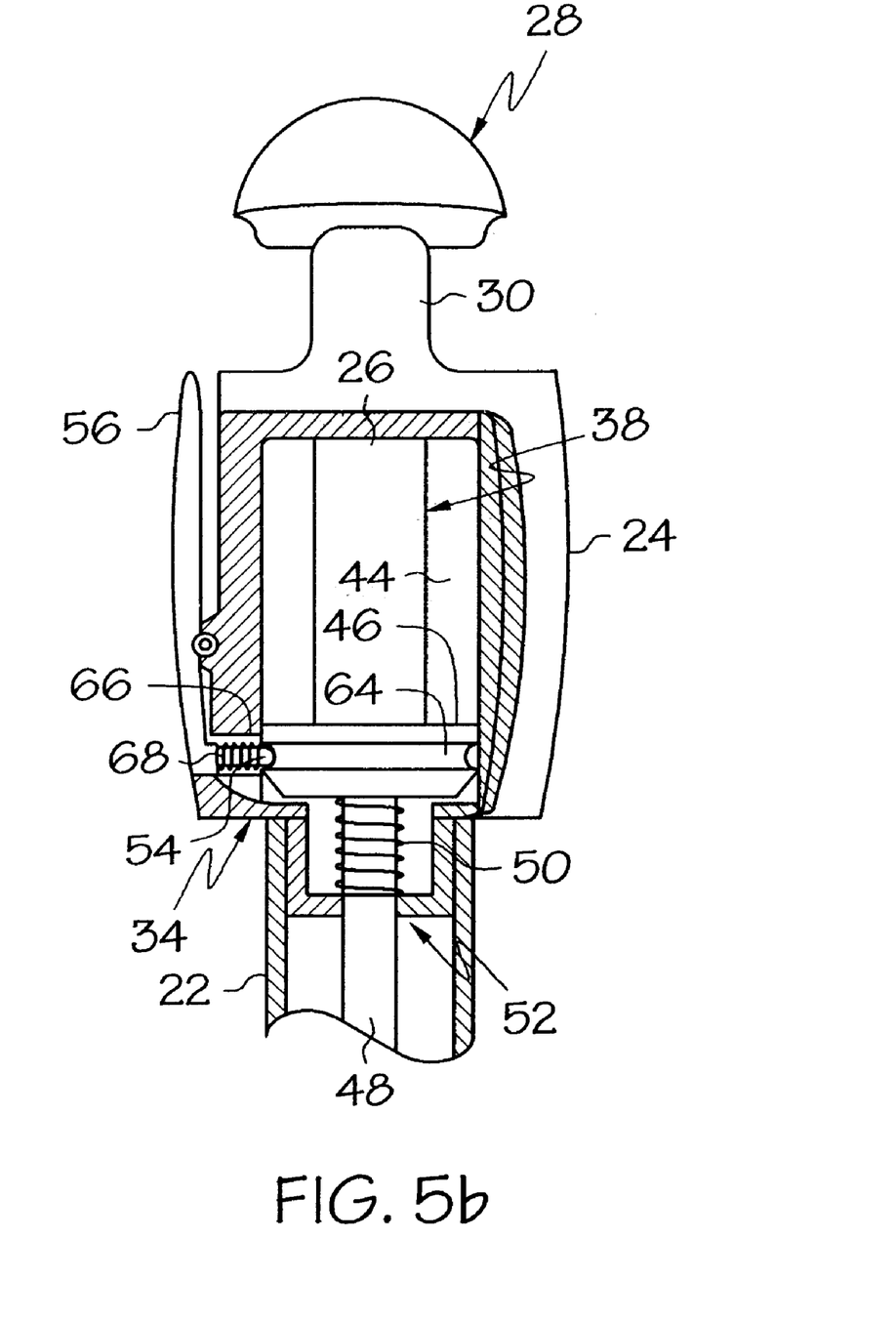
Figure 6:
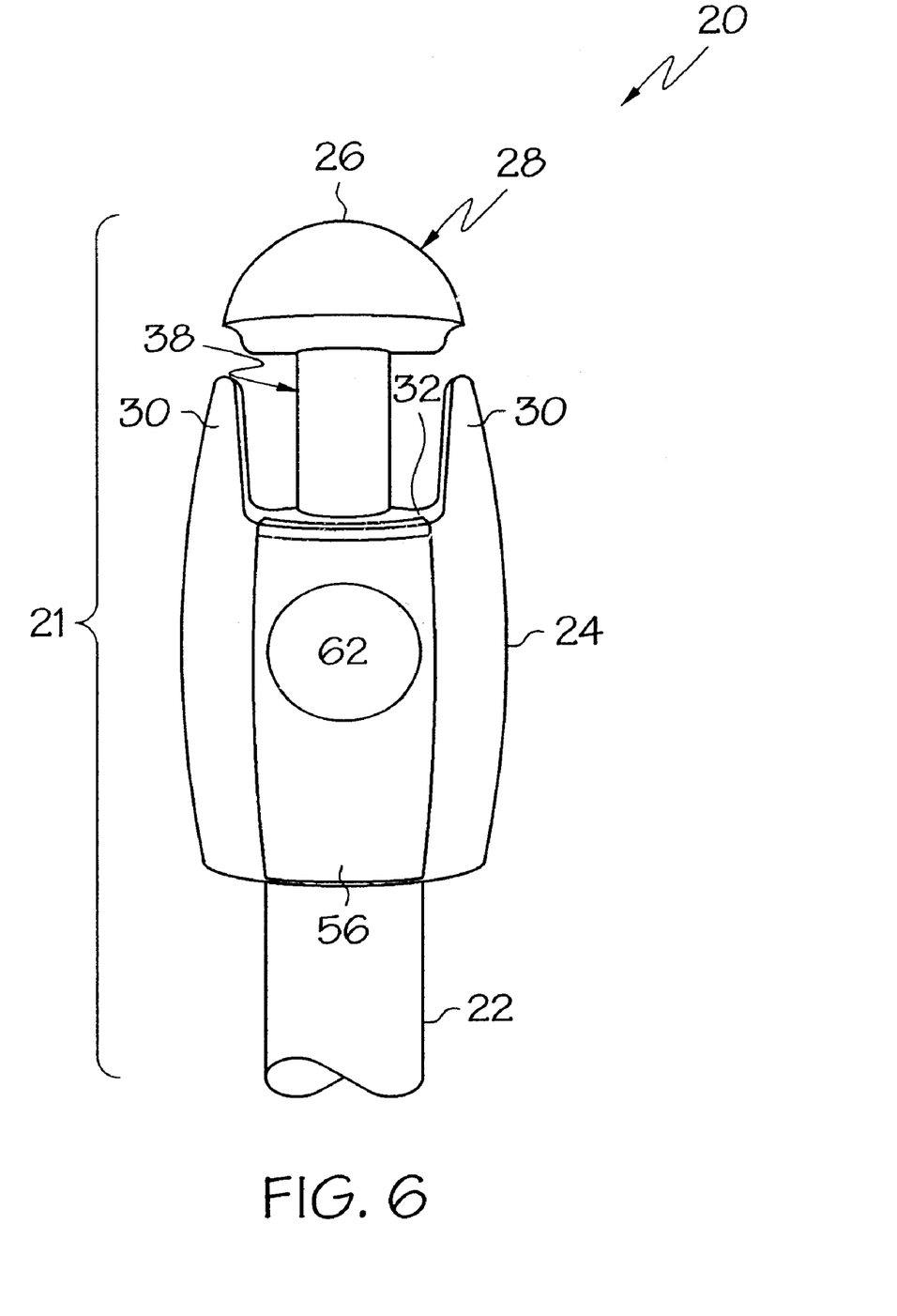
FIG. 6 is a front view of a holding assembly of an IV pole according to the present invention in a closed position.

In the embodiment of the holding device 21 illustrated by FIGS. 5a, 5b, and 6, a pop-up feature for the plunger 26 will be described. As for the embodiments illustrated by FIGS. 5a and 5b, the major difference between these embodiments is the manner by which the plunger 26 is retained or latched in the retracted position by an engagement member. It is to be appreciated that for other embodiments other latching methods may be used. In the embodiments of FIGS. 5a, 5b, and 6, the same features that were mentioned in regards to the embodiment of FIGS. 3 and 4, are labeled with like numbers, and for convenience, only the differences in this embodiment will be discussed.

In the embodiments shown by FIGS. 5a and 5b, the plunger 26 is part of a spring-loaded plunger subassembly. In these embodiments, the plunger 26 is mounted to a plate portion 46 of a guide rod 48 and is slidable with the guide rod against the bias of a guide rod spring 50. The plate portion 46, in addition to supporting the plunger 26, is sized such that it acts as stop preventing the stem portion 38 of the plunger 26 to exit completely from at least the plunger guide hole 36, which is best shown by FIG. 5a. The guide rod spring 50 is sized such that it is accommodated in chamber 44 and retained on the guide rod 48 between the plate portion 46 and a guide rod hole 52.

In the embodiment illustrated in FIG. 5b, the guide rod spring 50 is accommodated in a recess provided in the butt portion 34 of the head 24 such that the plate portion 46 of the guide rod 52 retracts in close proximity to the butt portion 34 within the chamber 44. The guide rod hole 52 is provided in the butt portion 34 of the head 24 in axial alignment with the plunger guide hole 36. The guide rod 48 extends from the guide rod-hole 52 coaxially through the spring 50 to the plunger 26. With the plunger 26 in the extended position, a portion of the guide rod 48 remains positioned in the guide rod hole 52, which is illustrated by the dashed-lines in FIG. 5a.

As previously mentioned, the plunger 26 and guide rod 48 are slidably movable against the bias of the guide rod spring 50. For the embodiment shown by FIG. 5a, manually compressing the guide rod spring 50 by pushing on the cap portion 28 of the plunger 26, engages the plate portion 46 of the guide rod 48 with a latching projection 54 provided on the interior surface of a push-button 56. The push-button 56 is mounted pivotally to the head 24 and biased against a spring (not shown) toward a retaining position. The latching projection 54 includes a sloping ridge 58 and an undercut 60. The sloping ridge 58 is angled such that the plate portion 46 of the guide rod 48 may slide over and slightly move the latching projection 54 away as the guide rod spring 50 is compressed with minimal resistance. As the plate portion 46 is moved below the latching projection 54, the push-button 56 retains the plunger 26 in the retracted position with the plate portion 46 engaged by the undercut 60 as illustrated by FIG. 6. When the push-button 56 is actuated, the undercut 60 of the latching projection 54 moves away from the plate portion 46, releasing the plunger to pop-up to the extended position. A thumb depression 62 may be provided to the exterior surface of the push button 56 for more convenient gripping.

For the embodiment shown by FIG. 5b, the plate portion 46 of the guide rod 48 is provided with a perimeter groove 64. The latching projection 54 of the push-button is accommodated in a horizontal through-bore 66 that opens in the cavity 44 of head 24. The latch projection 54 is biased against a spring 68, which maintains the latching projection 54 engaged in the groove 64 of the plate portion 46 holding the plunger 26 in the illustrated retracted position. Accordingly, pressing the push-button moves the latching projection 54 from the retaining position to a release position, which by releasing the guide rod spring 50 permits the plunger 26 to pop-up to the extended position as illustrated by FIG. 6.

In using the holding device 21 in the extended position (FIG. 5a), the cap portion 28 of the plunger 26 is held a length above the height of the projections 30 to allow IV fluid containers to be hung upon the projections. Pushing down on the cap 28 will place the plunger 26 in the retracted position (FIG. 6) with the latching projection 54 of the push-button 56 releasably engaging the plate portion 46 of the guide rod 48, thereby resetting the pop-up feature of the holding device 21. In the retracted position, the cap portion 28 either rests or is proximate to the projections 30 securing the IV fluid containers therein. Pressing the push-button, releases the latching projection 54 thereby springing the plunger 26, by the spring 50 expanding, to the extended position.

With regards to FIGS. 7–11, various embodiment of the IV pole 20 according to the invention are discussed. In the embodiment of the IV pole 20 shown by FIG. 7, the holding device 21 is provided at the end 23 of the elongated pole 22. The elongated pole 22 comprises an inner tube 70, an outer tube 72, a manually operable adjusting sleeve 74, and a socket assembly 76 located at the lower end of the outer tube 72. The outside diameter of the inner tube 70 is slightly smaller than the inside diameter of the outer tube 72 thereby permitting the inner tube to slide freely within the outer tube.

Figure 7:
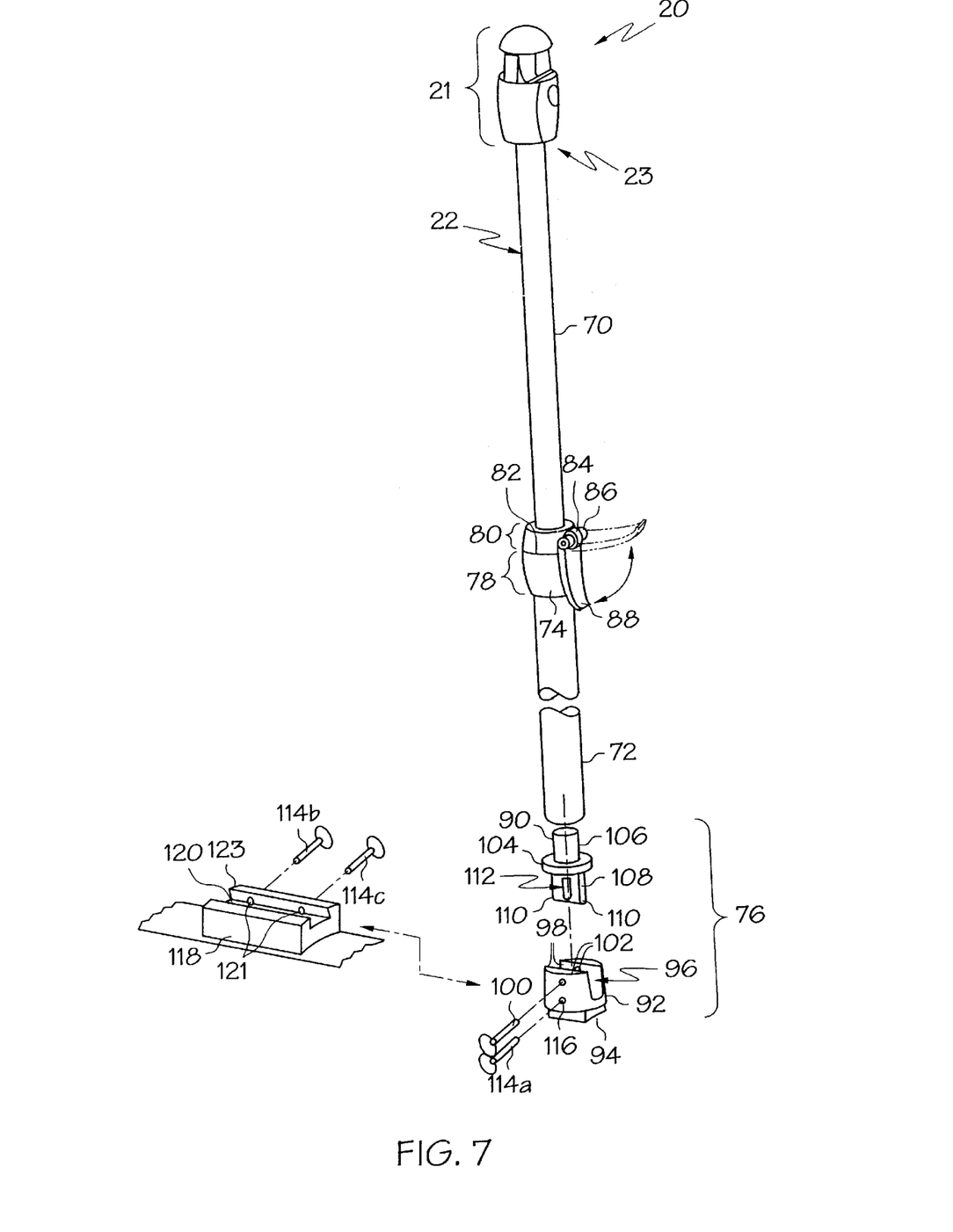
FIG. 7 is a perspective view, partially exploded, of an IV pole according to the present invention in an upright position.

The adjustable sleeve 74 at a lower portion 78 is mounted over the upper end of the outer tube 72. An upper portion 80 of the adjustable sleeve 74 is flexible along a portion of its circumference due to a slit 82 defining the upper portion into a pair of flexible radial arms 84 and 86. A lever 88 is pivotally mounted to the free ends of the arms 84, 86 and is used to releasably secure the inner tube 70 in place when located in a first position substantially parallel to the outer tube 72. Rotating the lever 88 from the first position to a second position substantially perpendicular to the sleeve 74, indicated by the dashed line, increases the circumference of the sleeve in the upper portion 80 such that the inner tube 70 may slide up or down freely. Rotating the lever 88 back down to the first position, draws the arms 84 and 86 of the sleeve 74 closer together thereby squeezing the inner diameter of the upper portion 80 of the sleeve 74 tightly against the outer circumference of the inner tube 70 securing the tube in place. Accordingly, the adjustable sleeve 74 is used to releasably secure the inner tube 70 in a selected vertical position with respect to the outer tube 72.

The socket assembly 76, which supports the pole 22 by its lower end in at least an upright condition, comprises a mounting plug 90, and a generally cylindrical collar 92 with preferably an integral dovetail base 94. For other embodiments, other conventionally known base configurations, such as for example a stand, may be used to support the IV pole 20 in the upright condition. The collar 92 has a cutout 96 extending into it from its upper edge diametrically across the collar. The cutout 96 is generally concave in shape and defines a pair of opposed walls 98. A bolt 100 is disposed in a pair of first holes 102 provided in the opposed walls 98 at a location above the bottom of the cutout such that the shank of the bolt extends approximately diametrically across the collar at approximately the midsection of the cutout.

The mounting plug 90 has near its center a radially outwardly projecting annular flange 104. Extending upwardly from the annular flange 104 is a very short cylindrical stub 106 having an outside diameter substantially equal to the inside diameter of the lower end of the outer tube 72. The stub 106 is disposed within the lower end of outer tube 72 such that the flange 104 is disposed against the lower end of the outer tube 72. The mounting plug 90 also includes an elongate projection 108 that extends downwardly from the flange 104. The projection is generally rectangular, and has a width that is slightly less than the distance between the opposed walls 98 of the collar 92. The outer edges 110 of the projection 108 is slightly rounded, and the projection 108 has a lengthwise slot 112 opening transversely through it such that the shank of the bolt 100 is slidably received within the slot.

When the pole 22 is in its upright condition, the annular flange 104 rests against the upper edge of the collar 92 with the shank of bolt 100 near the upper end of the slot 112 and spaced from the lower end 62 of slot 58. A first securing pin 114a is disposed in a second pair of holes 116. It is to be appreciated that the hole 116 on the unshown side is the same. The holes 116 are provided in the opposed walls 98 in a location below the first pair of holes 102 and above the bottom of the cutout 92 such that the shank of the pin 114a may pass through the slot 112 of the plug 90 with the flange 104 resting against the upper edge of the collar 92. Accordingly, cooperation of bolt 100, the pin 114a, and slot 112 prevents rotation of the outer tube 72.

Figure 8:
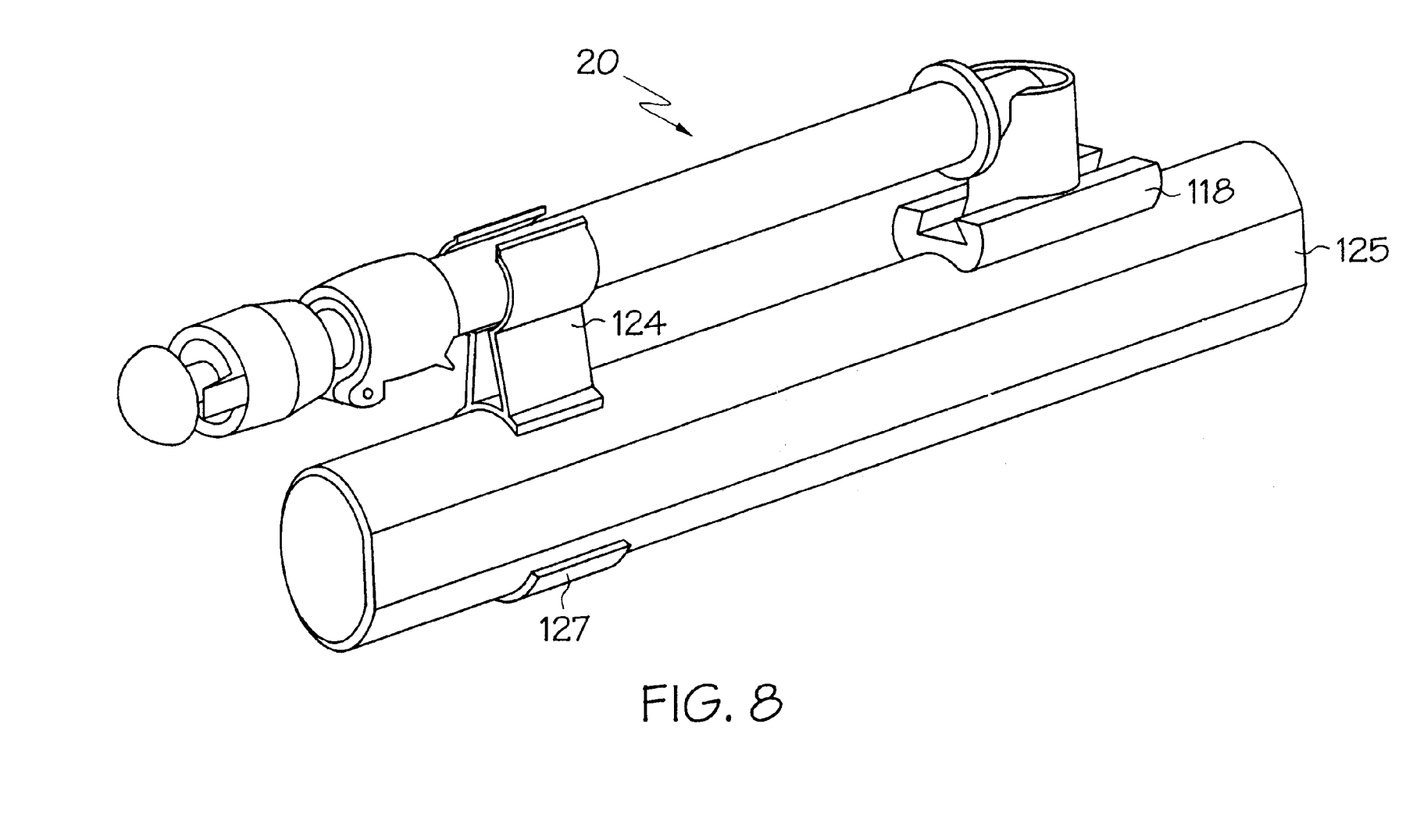
FIG. 8 is a perspective view of the IV pole of FIG. 7 shown in a stowed position.

The dovetail base 94 releasably mounts to a docking port 118 by sliding the collar 92 into an oppositely shaped mounting socket 120. Positioning second and third securing pins 114b and 114c, respectively, in holes 121 provided in a side wall 123 of the docking port 118 releasably secures the dovetail base 94 within the mounting socket 120. In one embodiment, the docking port 118 is mounted directly to a structural member 122, such as a side rail 125 of a stretcher or emergency cot, as illustrated in FIG. 8. As shown in FIG. 8, a support bracket 124 that easily clips onto the side rail 125 with a flexible C-clamp portion 127 may be used to provide extra support for the IV pole 20 when folded down parallel to the structural member in a stowed condition.

Figure 9A:
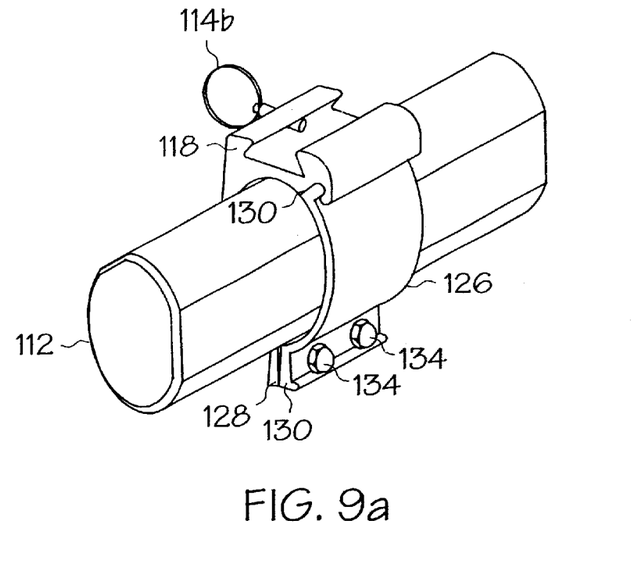
FIGS. 9a and 9b are perspective views of docking port/clamping arrangements of an IV pole according to the present invention.
Figure 9B:
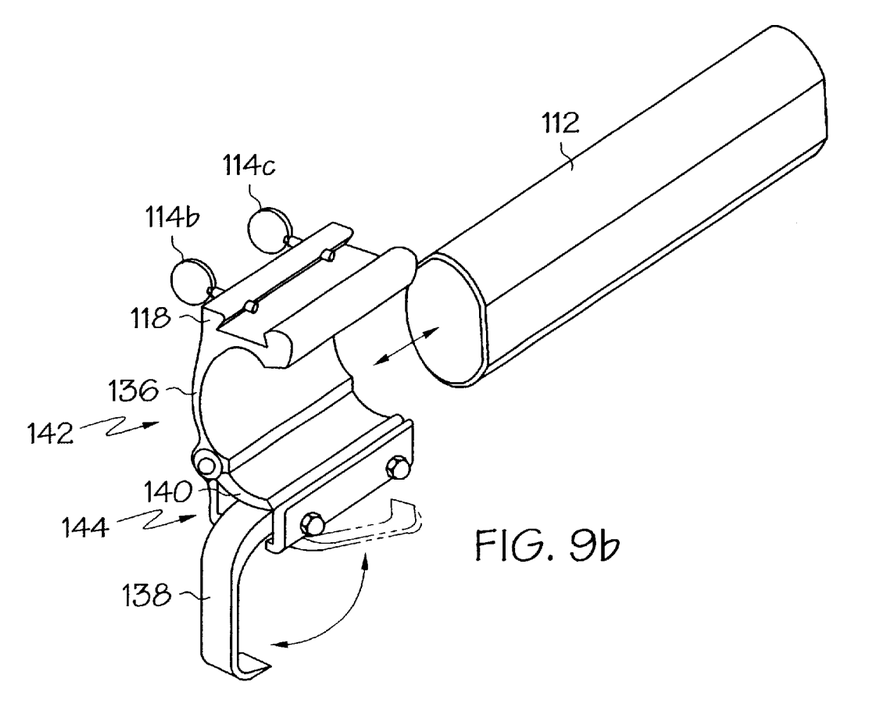

With reference to FIGS. 9a and 9b, embodiments of removably providing the docking port 118 to the structural member 112 according to the present invention are shown. For the embodiment of FIG. 9a, the docking port 118 is provided integral to an O-type clamping arrangement 126.

The O-type clamping arrangement 126 is formed of two halves 128 and 130 that interlock via a tongue and groove fitting 132, and held tightly on the structural member 112 by a pair of bolts 134. The advantage of this type of arrangement is the docking port 118 may be retrofitted and provided semi-permanently to structural members 112 of a structure, such as for example, various emergency cots, stretchers, vehicles, crash carts, hospital beds, and the like.

Referring to FIG. 9b, the docking port 118 is provided integral to a C-type clamp device 136 that permits the docking port 118 to be slidably engaged onto the structural member 112. Moving a handle 138 from a first position, shown by FIG. 9b, to a second position, indicated by a dashed-line, will cause a holding surface 140 of the C-type clamp device 136 to lift and to contact firmly against the structural member 112 thereby releasably securing the docking port 118 in place. An upper portion 142 of the C-type clamp 136 pivots relative to a lower portion 144 such that the C-type clamp may be easily removed from the structural member by positioning the handle 138 in the first position and pivoting the first portion 142 away from the structural member 112 relative to the lower portion 144. The advantage of such a clamping device is that the docking port may be easily and conveniently provided to and repositioned on structural members of various types of emergency cots, stretcher, crash carts, transport vehicles, hospital bed and the like.

Figure 10:
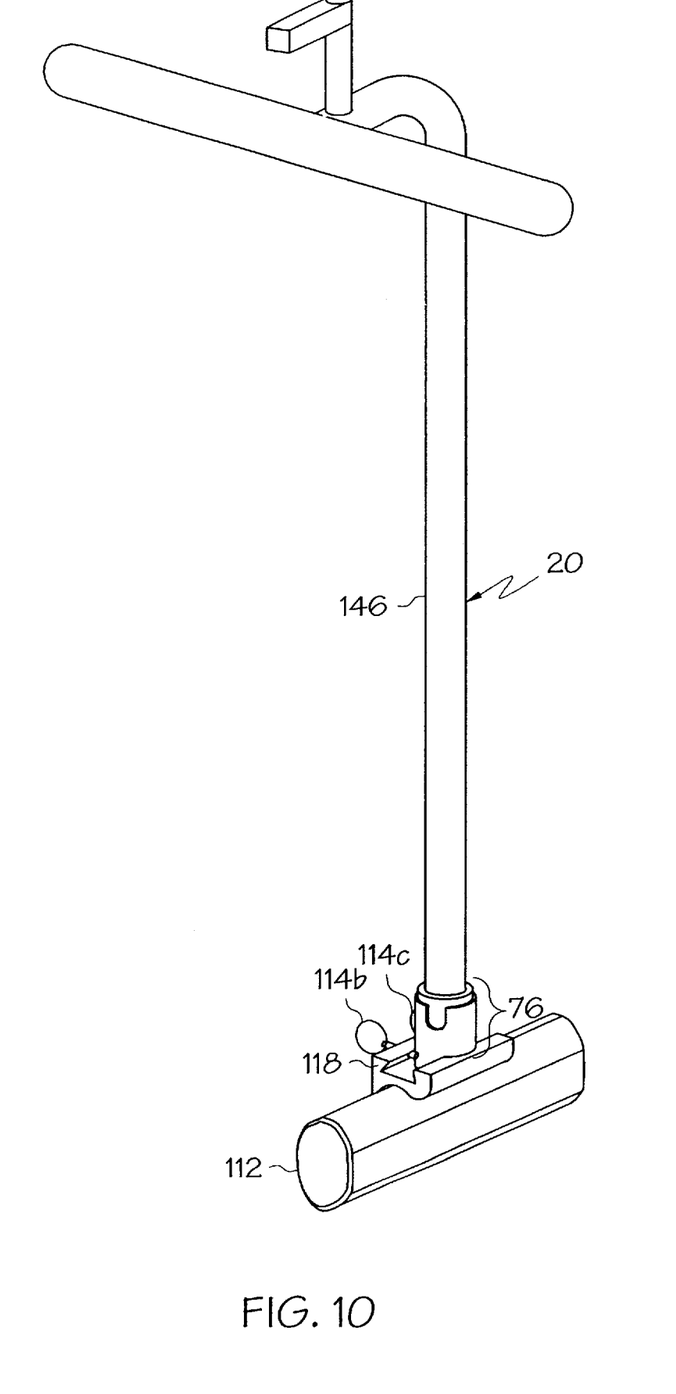
FIG. 10 is a perspective view of another embodiment of an IV pole according to the present invention.

Referring to FIG. 10, another embodiment of an IV pole 20 according to the present invention is shown. For this embodiment, at a lower end of a tubular support member 146 the dovetail support assembly 76 is provided such that the docking port 118 as previously mentioned releasably secures the IV pole 20 to the structural member 112. The support member 146 provides an integral cross bracket portion 148 which mat be used to hang intravenous fluid containers and other medical equipment.

Figure 11:
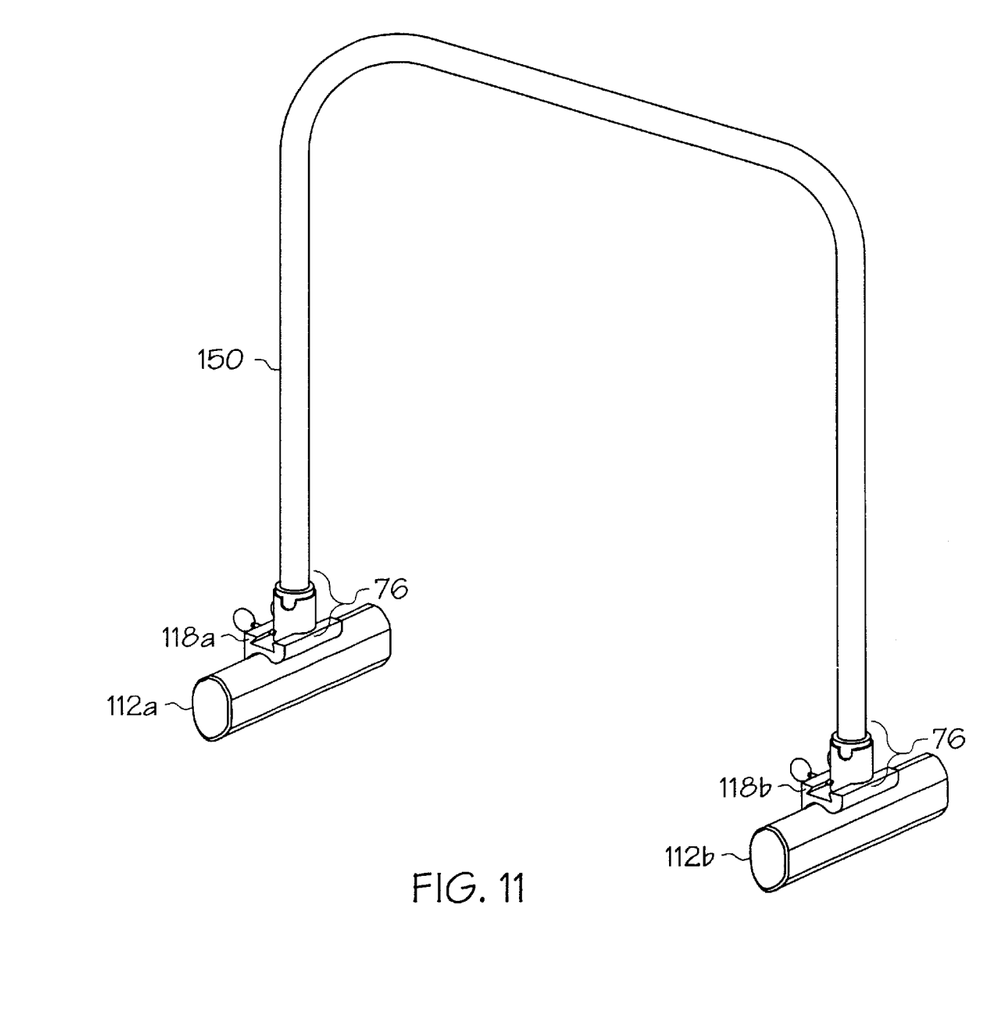
FIG. 11 is a perspective view of still another embodiment of an IV pole according to the present invention.

In still another embodiment of the IV pole 20 according to the present invention, a tubular bar 150 is provided which spans between two structural members 112a and 112b, as illustrated by FIG. 11. At each end of the bar 150 a dovetail support assembly 76 is provided in the same manner as explained above such that the ends of the bar 150 may by releasably secured in docking ports 118a and 118b provided on the structural members 112a and 112b.

In the foregoing specification, the invention has been described with reference to specific exemplary embodiments thereof It will, however be appreciated that various modifications and changes, such as replacing the conventional holding brackets on conventional IV poles with the holding device of the invention, may be made thereto without departing from the broader spirit and scope of the invention as set forth in the appended claims. The specification and drawings are, accordingly, to be regarded in an illustrative rather than a restrictive sense.

What is claimed is:

1. A holding device for securing at least one intravenous fluid supply to a fixture, said holding device comprising:
   a head having a proximate end portion configured to support the at least one intravenous fluid supply, and a distal end portion configured to be mounted to the fixture, said head defining an internal chamber and a guide hole provided in said proximate end portion, said chamber is in communication with said guide hole; and
   a plunger having a cap portion, said plunger slidably mounts in said chamber and extends through said guide hole such that said plunger is operable between an extended position in which said cap potion of said plunger extends a distance above said proximate end portion of said head and a retracted position in which said cap portion secures the at least one intravenous fluid supply to said holding device.

2. The holding device as recited in claim 1 wherein said proximate end portion of said head comprises a pair of opposed projections.

3. The holding device as recited in claim 1 wherein said plunger is spring-biased toward the extended position.

4. The holding device as recited in claim 3 wherein said plunger is releasably securable in said retracted position.

5. The holding device as recited in claim 4, further comprising a push-button operably mounted to said head, said push-button when pushed permits said plunger to pop-up from said retracted position to said extended position.

6. The holding device as recited in claim 2 wherein said guide hole is centrally located between said pair of projections, and wherein said plunger when in said retracted position said cap portion of said plunger engages said pair of projections.

7. The holding device as recited in claim 1 wherein the fixture is a tube of an IV pole, and said distal end portion mounts to an end of said tube.

8. An IV pole for supporting fluid containers above a structure, said IV pole comprising:
   an elongated pole having a first end and a second end;
   a holding device mounted to said first end, said holding device having upwardly extending projections and a plunger with a cap portion, said plunger is movable between an extended position, in which said cap portion is a distance from said projection such that the fluid containers may be hung upon said projections, and a retracted position in which said cap portion is in close proximity to said projections such that said hung fluid containers are releasably secure upon said projections; and
   a support mounted at said second end for holding said IV pole in an upright condition.

9. The IV pole as recited in claim 8, wherein said elongated pole comprises an inner tube, an outer tube, and an adjusting sleeve used to releasably secure the inner tube in a selected vertical position with respect to the outer tube.

10. The IV pole as recited in claim 8, wherein said support comprises a mounting plug having first and second ends, a collar, and a docking port provided to the structure, said first end of said mounting plug mounted to said outer tube, said second end of said mounting plug rotatably mounted to said collar such that said IV pole is movable between the upright condition and a stowed condition, and said collar releasably secured to said docking port.

11. The IV pole as recited in claim 10, wherein said collar includes an integral dovetail base, and said docking port is oppositely shaped to receive shaped dovetail base.

12. The IV pole as recited in claim 10, wherein said docking port further comprises an O-type clamp portion such that said docking port is releasably secured to the structure.

13. The IV pole as recited in claim 10, wherein said docking port further comprises a C-type clamp portion such that said docking port is releasably secured to the structure.

14. The IV pole as recited in claim 10, further comprising an additional support provided to the structure to provide additional support to the IV pole when in the stowed condition.

15. The IV pole as recited in claim 8, wherein the plunger is spring-biased toward said extended position.

16. The holding device as recited in claim 15, plunger is releasably securable in said retracted position.

17. The holding device as recited in claim 16, further comprising a push-button operably mounted to said head, said push-button when pushed permits said plunger to pop-up from said retracted position to said extended position.

18. The holding device as recited in claim 8 wherein said plunger when in said retracted position said cap portion of said plunger engages said pair of projections.

19. An IV pole for supporting fluid containers above a structure, said IV pole comprising:

a. an elongated pole having first and second ends;

a collar with an integral dovetail base;

a docking port provided to said structure and having an oppositely shaped channel configured to slidably receive said dovetail base of said collar, said collar releasably secured to said docking port; and a mounting plug having first and second ends, said first end of said mounting plug mounted to said first end of said pole, said second end of said mounting plug rotatably mounted to said collar such that said IV pole is movable between an upright condition and a stowed condition.

20. The IV pole as recited in claim 19, further comprising:

a second collar with an integral dovetail base;

a second docking port provided to said structure and having an oppositely shaped channel configured to slidably receive said dovetail base of said second collar, said second collar releasably secured to said second docking port; and a second mounting plug having first and second ends, said first end of said second mounting plug mounted to said second end of said pole, said second end of said second mounting plug rotatably mounted to said second collar.

* * * * *

UNITED STATES PATENT AND TRADEMARK OFFICE
CERTIFICATE OF CORRECTION

PATENT NO. : 6,431,505 B1
DATED : August 13, 2002
INVENTOR(S) : Chinn et al.

It is certified that error appears in the above-identified patent and that said Letters Patent is hereby corrected as shown below:

Column 8,
Line 1, reads as "potion of said" should read -- portion of said --.

Column 9,
Line 1, reads as "15, plunger is" should read -- 15, wherein said plunger is --.

Signed and Sealed this

Eleventh Day of February, 2003

JAMES E. ROGAN
*Director of the United States Patent and Trademark Office*